United States Patent
Underhill et al.

(10) Patent No.: US 7,335,190 B2
(45) Date of Patent: Feb. 26, 2008

(54) METHOD OF PROVIDING A SERIES OF DISPOSABLE ABSORBENT ARTICLES TO CONSUMERS

(75) Inventors: Richard Louis Underhill, Neenah, WI (US); Rebecca Suzanne Walter, Hortonville, WI (US); Christopher Peter Olson, Neenah, WI (US); Shirlee Ann Weber, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 11/051,828

(22) Filed: Feb. 4, 2005

(65) Prior Publication Data

US 2005/0137543 A1 Jun. 23, 2005

Related U.S. Application Data

(63) Continuation of application No. 10/025,203, filed on Dec. 19, 2001, now Pat. No. 6,884,238.

(51) Int. Cl.
*A61F 13/15* (2006.01)
*A61B 19/02* (2006.01)
*B65D 73/00* (2006.01)

(52) U.S. Cl. .......................... 604/385.01; 604/385.04; 206/494; 206/438

(58) Field of Classification Search ........... 604/385.01; 206/438, 494
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,340,563 A | 7/1982 | Appel et al. |
| 4,663,220 A | 5/1987 | Wisneski et al. |
| 4,938,753 A | 7/1990 | Van Gompel et al. |
| 4,940,464 A | 7/1990 | Van Gompel et al. |
| 5,007,906 A | 4/1991 | Osborn, III et al. |
| 5,046,272 A | 9/1991 | Vogt et al. |
| 5,062,839 A | 11/1991 | Anderson |
| 5,104,116 A | 4/1992 | Pohjola |
| 5,224,405 A | 7/1993 | Pohjola |
| 5,226,992 A | 7/1993 | Morman |

(Continued)

FOREIGN PATENT DOCUMENTS

EP  0 217 032 B1  2/1992

(Continued)

*Primary Examiner*—Jacqueline F. Stephens
(74) *Attorney, Agent, or Firm*—Pauley Petersen & Erickson

(57) ABSTRACT

A method of providing a series of types of pant-like garments and corresponding information to consumers. The series includes two or more pant-like garments, each of the garments corresponding to a stage of toilet training. Each of the garments in the series may differ from one another in terms of absorbent capacity, size, and/or features. The information provided to the consumer helps the consumer discern which garment from the series is most appropriate for a child in a specific stage of the toilet training process.

34 Claims, 3 Drawing Sheets

U.S. PATENT DOCUMENTS

| | | |
|---|---|---|
| 5,649,914 A * | 7/1997 | Glaug et al. ................. 604/361 |
| 5,658,268 A | 8/1997 | Johns et al. |
| 5,702,377 A | 12/1997 | Collier, IV et al. |
| 5,839,585 A | 11/1998 | Miller |
| 5,897,542 A | 4/1999 | Lash et al. |
| 5,964,743 A | 10/1999 | Abuto et al. |
| 6,079,562 A | 6/2000 | Bauer et al. |
| 6,229,061 B1 | 5/2001 | Dragoo et al. |
| 6,229,063 B1 | 5/2001 | Shimoe et al. |
| 6,250,929 B1 | 6/2001 | Kolb et al. |
| 6,454,095 B1 | 9/2002 | Brisebois et al. |
| 6,648,864 B2 | 11/2003 | Ronn et al. |
| 6,763,944 B2 | 7/2004 | Ronn et al. |
| 2003/0135186 A1 | 7/2003 | Olson et al. |
| 2004/0010240 A1 | 1/2004 | Ronn et al. |
| 2004/0030308 A1 | 2/2004 | Ronn et al. |

FOREIGN PATENT DOCUMENTS

| | | |
|---|---|---|
| EP | 0 661 031 A2 | 7/1995 |
| EP | 0 454 105 B1 | 11/1995 |
| WO | 96/06587 | 3/1996 |
| WO | 96/10381 | 4/1996 |

* cited by examiner

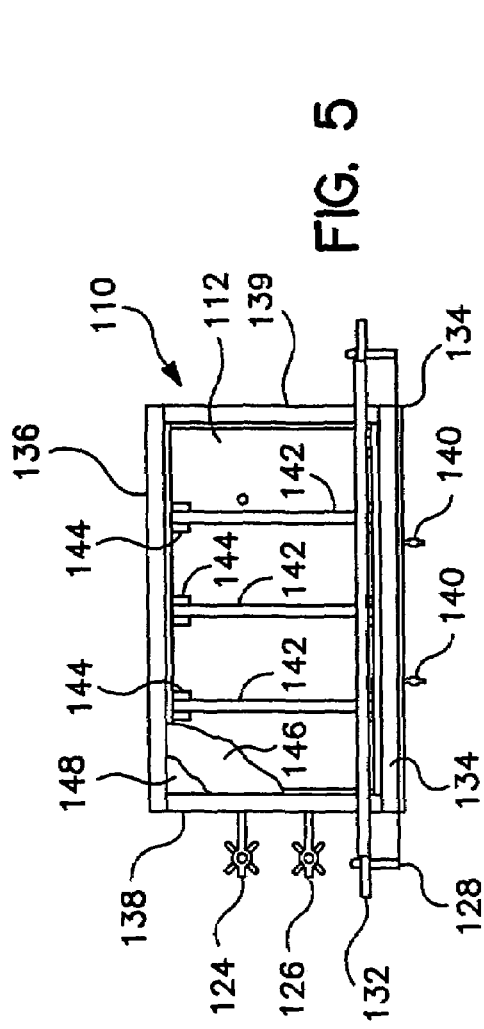
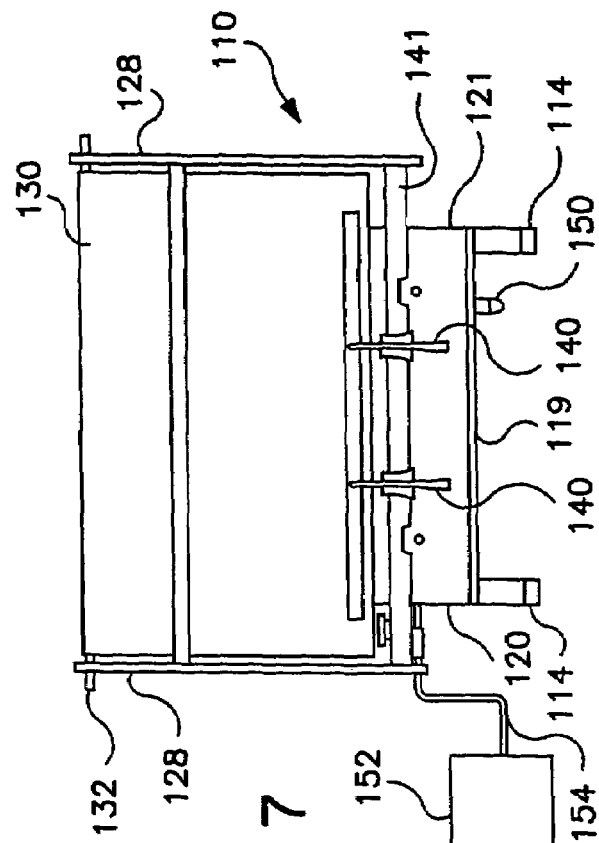
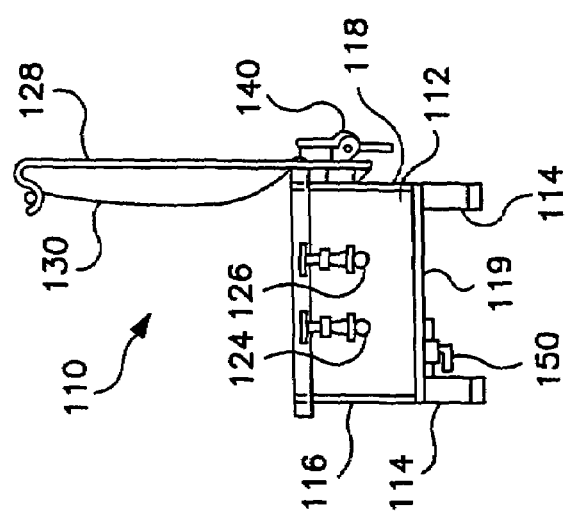

METHOD OF PROVIDING A SERIES OF DISPOSABLE ABSORBENT ARTICLES TO CONSUMERS

RELATED APPLICATION

This application is a continuation of U.S. patent application Ser. No. 10/025,203, filed 19 Dec. 2001 now U.S. Pat. No. 6,884,238. The disclosure of the prior application is incorporated herein by reference.

BACKGROUND OF THE INVENTION

This invention is directed to a method of combining a series of types of disposable undergarments having varying degrees of absorbent capacity and toilet training features with information that corresponds to the applicability of the undergarments in view of the changing needs and abilities of caregivers and toilet training children.

The process of toilet training a child can be frustrating for the child as well as for the caregiver. The ability to control one's excretory functions involves both physiological and psychological developments. These developments take time.

As children increase in age and personal development, their ability to discern changes in their surrounding environment increases. A key area of change for toilet training children is their ability to notice tactile changes when urinating or defecating in a disposable undergarment. A child's caregiver is typically the best judge of the child's readiness for toilet training and is typically aware of reasonable expectations of the child's abilities in various settings and at various times. For early stage trainers, the children are starting to learn the difference between the tactile feeling of wet and dry, and do not have the bowel and bladder control needed to stop urinating in the disposable undergarment they are wearing. As children make progress in toilet training their tactile perceptions increase and their bowel and bladder control improve.

As a child makes progress in toilet training, he or she stops wearing diapers and may begin wearing training pants or cloth undergarments. Cloth underwear is not preferred by many caregivers due to the inconvenience of inevitable accidents. Both diapers and training pants are typically designed to contain multiple insults. As a child progresses through the toilet training process, they learn to control their bowels and bladder and can become capable of identifying when an insult has occurred in their training pant. However, high capacity absorbent products that are able to fully absorb a child's insults may prevent the child from noticing when an insult has occurred. As a result, less absorbent capacity is needed in training pants during the later toilet training stages. Furthermore, it can be desirable to signal to the child a change of expectations with respect to control of bodily functions.

If a training pant has a high absorbent capacity, it is suitable for the early stages of toilet training, but it may not motivate the child to finish toilet training if the child knows that he or she can continue to issue multiple insults without any negative consequences. If a training pant has a low absorbent capacity, it is suitable for the late stages of toilet training during which time the training pant acts as a safety net in case the wearer accidentally issues one insult, but it may discourage a child in the early stages of toilet training if he or she does not have to ability to control their insults yet and the training pant is unable to contain all of their waste.

There is a need or desire for a series of training pants and corresponding information that pertains to the toilet training process, the combination of which addresses a child's needs and abilities as the child progresses through the toilet training process.

SUMMARY OF THE INVENTION

In response to the discussed difficulties and problems encountered in the prior art, a new method of providing a series of types of disposable training pants to consumers has been discovered.

The present invention is directed to a method providing a series of at least three types of disposable undergarments that provide different levels of absorbency to correspond to the progress made by toilet training children, along with information provided to the caregiver to help the caregiver determine which undergarment is appropriate for a particular child.

Because children in the earlier stages of toilet training have not yet developed the needed levels of bowel and bladder control or physiological awareness or anticipation of the need to void, a product with a high absorbency level to contain one or more voids in the pant is appropriate in the early stages of toilet training. Appropriate undergarments for the later stages of training are designed with less absorbency making them saturated with less liquid. As the product becomes saturated the child will feel wet. Garments with less absorbency help the child realize the wetness and stop voiding in the product while the garment still provides leakage protection against single-insult accidents.

The series of undergarment types can include multiple undergarments having different absorbent capacities. For example, the series can include an early stage garment having an absorbent capacity sufficient to contain multiple insults and a late stage garment having an absorbent capacity sufficient to contain only one insult. Additionally, the series can also include one or more intermediate garments having absorbent capacities in between the capacities of the early stage and late stage garments, or absorbent capacities even greater than the capacity of the early stage garment.

All of the garments in the series may have the same design and differ only in terms of the absorbent capacity, and possibly size. Alternatively, the garments may differ in terms of features as well. For example, any number of the garments in the series may have refastenable side seams. Likewise, any number of the garments in the series may have permanently bonded side seams. Furthermore, any number of the garments in the series may be unisex or gender-specific.

Additional features that may be present in some or all of the garments in the series to make the training process more convenient, efficient or understandable include sensory signals, such as tactile wetness indicators or visual wetness indicators. For example, since a child in the early stages of toilet training has not yet developed tactile detection of wet and dry, visual wetness indicators may help the child identify a need for a clean training pant early on in the toilet training process. Later on in the toilet training process, after the child has developed tactile awareness, a tactile wetness indicator, such as a wet liner, may be appropriate to enhance the child's wetness detection.

With the foregoing in mind, particular embodiments of the invention provide a method of providing a series of types of disposable training pants to consumers that address a child's needs as the child progresses through the toilet training process.

BRIEF DESCRIPTION OF THE DRAWINGS

FIGS. 5-7 representatively show a partially cut away top view, a side view, and a rear view, respectively, of a Saturated Capacity Tester.

DEFINITIONS

Figure 1:
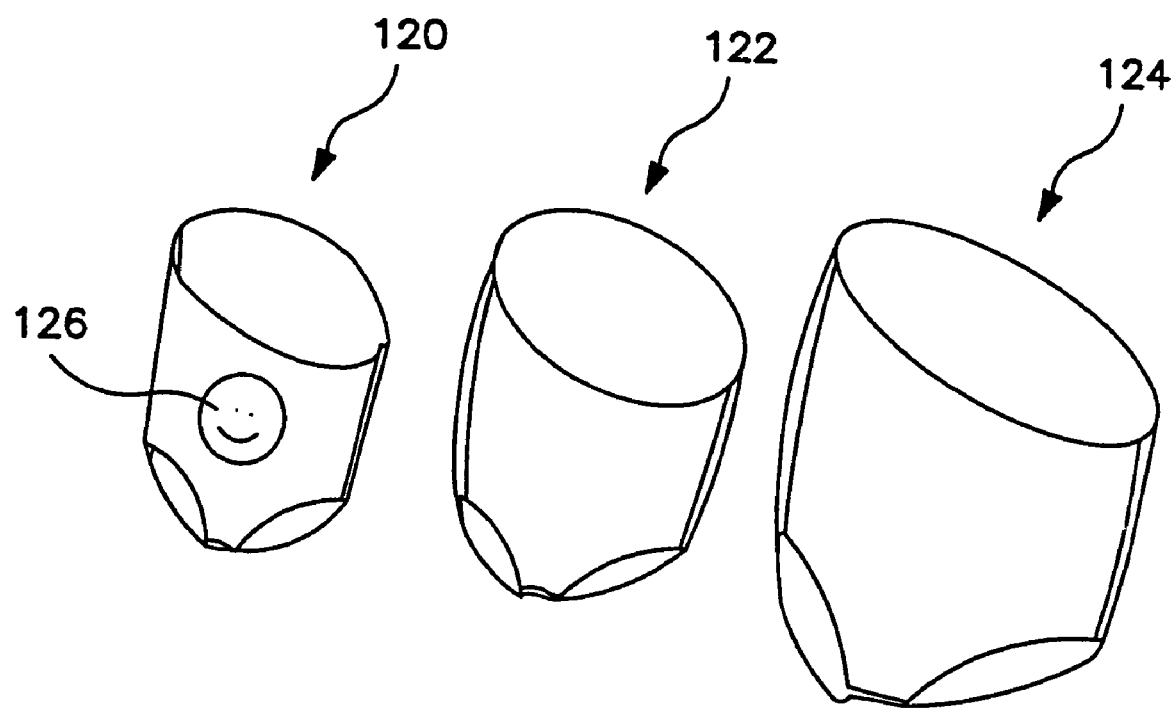
FIG. 1 is a perspective view of a series of absorbent garments, according to one embodiment of this invention.

Within the context of this specification, each term or phrase below will include the following meaning or meanings.

"Absorbent capacity" refers to the maximum volume of liquid that can be absorbed by a material without any runoff occurring.

"Anticipated single insult volume" refers to the near-maximum amount of urine or other exudates that can be expected to be expelled during a single void or insult. More specifically, based on an average of acquired data, the anticipated single insult volume is three standard deviations higher than the mean single insult volume.

"Audio wetness indicator" refers to a device that signals the detection of wetness via a sense of sound.

"Behavioral techniques" include demonstrating how you use the toilet; reminding the child to use the potty; limiting or keeping track of child's intake of fluids; running water while child is seated; praising for toileting progress; providing cloth training pants; providing disposable training pants; providing potty seat/chair; letting child decide when to go; not allowing diapers once started training; giving rewards for success; firm and consistent approach; verbal teaching and explanation of toilet training; dressing the child in few/no clothes; disciplining the child; providing children's underwear/panties; placing on potty/toilet at certain intervals; monitoring child's behavior; having your child sit on the potty for a specified time period; using older children as role models (home or daycare); encouraging your child to be a "Big Kid;" and using toilet training videos and books to motivate your child.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Disposable" refers to garments or articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabric" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Gender-specific" describes an item that is designed to be more suitable for one gender, either male or female, than the other.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid-impermeable," when used to describe a layer or laminate means that liquid such as urine will not pass through the layer or laminate under ordinary use conditions in a direction generally perpendicular to the plane of the layer or laminate at the point of liquid contact.

"Liquid-permeable," refers to a layer or laminate that is not liquid impermeable.

Figure 3:
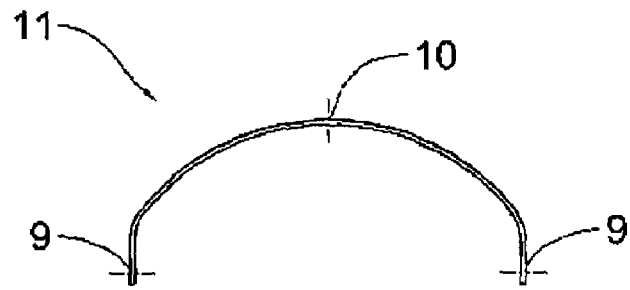
FIG. 3 is a plan view of the absorbent garment of FIG. 2 in a partially disassembled, stretched flat state, and showing the surface of the garment that faces away from the wearer when the garment is worn, according to one embodiment of this invention.
Figure 4:
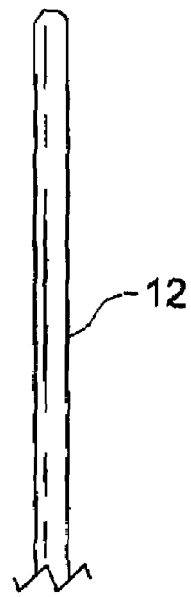
FIG. 4 is a plan view of the absorbent garment of FIGS. 2 and 3 in a partially disassembled, stretched flat state, and showing the surface of the garment that faces the wearer when the article is worn, and with portions cut away to show the underlying features, according to one embodiment of this invention.

"Longitudinal" and "transverse" have their customary meaning, as indicated by the longitudinal and transverse axes depicted in FIGS. 3 and 4. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joint or junction. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Series" refers to a set of two or more items having a similar appearance and/or functionality, with at least one feature, such as absorbent capacity, evolving from one state, e.g. high absorbency, to another, e.g. low absorbency, throughout the items in the series.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 1.2 times its initial (unstretched) length in at least one direction.

"Superabsorbent" or "superabsorbent material" refers to a water-swellable, water-insoluble organic or inorganic material capable, under the most favorable conditions, of absorbing at least about 15 times its weight and, more desirably at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Tactile wetness indicator" refers to a device that signals the detection of wetness via a sense of touch.

"Thermoplastic" describes a material that softens when exposed to heat and which substantially returns to a non-softened condition when cooled to room temperature.

"Toilet training aids" include: potty training story books for children; potty training guide books for parents; potty training videotapes for children; progress charts with stickers; stickers alone as rewards; potty training dolls; miniature toilets; potty training flash cards; potty training tip sheets; potty training brochures and pamphlets; reward items, such as stickers, crayons, candy, toys or the like; urine targets; potty training diplomas; starter kits containing a combination of these items; potty chairs; musical potty chairs; wetness awareness devices, such as musical alarms, "feel wet" liners, or the like; and toilet paper with children's graphics.

"Unisex" describes an item that is designed to be equally suitable for both genders, male and female.

"Visual wetness indicator" refers to a device that signals the detection of wetness via a sense of sight.

"Wetness indicator" refers to a device that signals the detection of wetness via a sensory device, such as by sight, sound, smell, or touch.

These terms may be defined with additional language in the remaining portions of the specification.

DETAILED DESCRIPTION OF THE INVENTION

The present invention is directed to a method of providing a series of two or more types of disposable undergarments and corresponding information pertaining to the toilet training process. The information provided in this method is intended to provide a parent or caregiver, hereinafter simply referred to as a caregiver, with some guidance on how to select an appropriate absorbent article for a child during the toilet training process based on the caregiver's knowledge of the child's abilities, attention span, and other personal characteristics that may have a bearing on the child's toilet training progress.

The principles of the present invention can be incorporated into a series of any suitable disposable absorbent article types, or a series of a combination of any suitable disposable absorbent article types. Examples of such suitable articles include, but are not limited to, pant-like articles such as diapers and training pants. Suitable articles may also include pads or liners or other suitable absorbent articles that can be inserted into pants. For ease of explanation, the description hereafter will be in terms of a series of children's training pants.

Referring to FIG. 1, a series of types of pant-like disposable absorbent garments or articles, such as training pants 20, is illustrated. For purposes of illustration, the series includes three training pants 20, but a series of training pants in accordance with the present invention can include as few as two training pants and as many different training pants as necessary to address the needs of a child during various stages of toilet training.

Each of the pants 20 in the series may differ from the others in terms of absorbent capacity, size, and/or special features. More particularly, an early stage training pant 120 suitably has a larger absorbent capacity than a later stage training pant 124, while a middle stage training pant 122 may have an absorbent capacity between the early stage and late stage absorbent capacities or even greater than the early stage absorbent capacity. Thus, the absorbent capacity may be inversely related to a child's bladder control ability and can provide a motivation to the child to exercise that control.

Higher absorbent capacities are suitable in early stage training pants 120 because children in the earlier stages of toilet training have not yet developed bowel and bladder control or wetness perception. Therefore, early stage training pants 120 are designed to contain multiple voids. As children make progress in toilet training, their physiological perceptions increase and their bowel and bladder control improve. Later stage training pants 124 are designed with less absorbency such that the training pants become saturated with less liquid compared to the early stage training pants 120. As the training pant becomes saturated, the child will feel wet. When a child can detect wetness, the child is likely to stop voiding in the training pant if he or she can do so. Each of the training pants in the series provides leakage protection commensurate with the respective absorbent capacity.

Essentially, later stage training pants within the series provide a child with a one-chance opportunity, that is, the later stage training pants can be single void training pants designed to contain less than twice an anticipated single insult volume, or even less than a single anticipated insult volume. With the absorbent capacity being so low, the child may face the consequence of a minor leakage if the child does insult the pant, which is much less severe in terms of clean-up compared to cloth training pants. This single void training pant concept acts as a safety net for the caregiver inasmuch as the child's abilities are not simply allowed to regress due to inconvenience as they might be if the caregiver had to resort to applying a high-absorbency pant for times when the caregiver is unable to be actively coaching the child. The low absorbent capacity pant is also a potentially useful tool for caregivers who choose to use cloth pants at home, but wish to avoid the inconvenience of carrying a total change of clothes when out of the house with the child.

As another embodiment of the invention, the series may include garments with increased absorbency designed for use during various times within the later stages of toilet training when a need for increased absorbency is foreseeable, such as at night, or during certain excitable events, or over longer than normal durations.

As illustrated in FIG. 1, overall size of the training pants within the series may vary. Since children continue to grow during the toilet training process, the size of the garments may increase from the early stage training pant 120 through the later stage training pant 124. Consequently, as the absorbent capacity of the training pant decreases, the size of the training pant 20 may increase. Alternatively, each of the training pants in the series may be of a single size designed to accommodate a user who may be increasing in size during the training process.

For purposes of the present invention, the "size" of one garment type relative to another garment type refers to a difference in the size of their waist openings when extended by a force of 2,000 grams. In particular, waist size can be determined by placing a pant on upper and lower pins of a tensile tester equipped with a suitable operating and data acquisition system, for example, MTS tensile tester model Synergie 200 Test Bed and MTS TestWorks® for Windows software version 3.10, both available from MTS® Systems Corporation, Research Triangle Park, N.C. U.S.A. The tensile tester jaws are separated until reaching 2,000 grams of tension (or a maximum load value that can be experienced by the sample without causing the sample to tear or otherwise come apart). At that point the gage length is recorded. The waist size can be calculated by multiplying the gage length at that tension by 2, and adding one half the circumference of the upper pin and one half the circumference of the lower pin. Waist size is tested under standard ASTM laboratory conditions, and is desirably an average of values from at least 3 pants. Hence, the series of training pants may include small size garments having an average waist size that is less than larger size garments.

In a particular embodiment of the invention, the series may include at least three different types of disposable pant-like garments, with at least two of the garments targeted to fit wearers in a lower weight range, namely of a smaller size, than at least one of the other garments in the series. In this embodiment, the garment or garments targeted to fit wearers in a higher weight range, namely the larger garments, have a lower absorbent capacity than the smaller garments.

In another particular embodiment of the invention, the series includes at least two series, or sub-series, of disposable pant-like garments. Each of the garments within a single series or sub-series is a different size, such that if there are three garments in a first series there are three garments in three different sizes. The garments in a second series are the same sizes as the garments in the first series, however, all of the garments in the first series have a higher absorbent capacity than the garments in the second series. This embodiment is designed to provide absorbent garments in a wide range of sizes that are each available in a range of absorbent capacities suitable throughout various stages of toilet training, since children become ready to toilet train at different times from child to child, and not all children are the same size at any single stage of the toilet training process.

Each of the pants in the series may differ from pant to pant in terms of absorbency, design, size and/or features. For example, the pants 20 can be either unisex or gender-specific, or the earlier stage training pants 120 can be unisex while the later stage training pants 124 can be gender-specific. Other features include a pull-on design as opposed to a refastenable design, explained in detail below. Additional features that may make the series of training pants more convenient, efficient, or understandable include wetness indicators. A wet liner or other tactile wetness indicator is particularly suitable for inclusion in later stage training pants 124 which are typically worn when a wearer has developed a recognition of the feeling of wetness. A visual wetness indicator 126 may be particularly suitable for inclusion in earlier stage training pants 120 which are typically worn when a wearer may not have developed a recognition of the feeling of wetness but is likely to be able to see a wetness indicator, such as a graphic, disappear when wetness occurs. Other types of wetness indicators may include audio wetness indicators in which a sound is made when wetness is detected, or olfactory wetness indicators in which a scent is emitted when wetness is detected.

In carrying out the method of the invention, information regarding correlations between a child's readiness and the appropriate training pant from the series may be made available to consumers contemplating the purchase of one of the types of training pants in the series. An example of such information is described in detail in U.S. Pat. No. 6,250,929, issued to Kolb, et al., hereby incorporated by reference.

More particularly, in terms of information provided for the purchaser, the key to communicating is helping the caregiver know when the child is ready to switch to lower absorbency training pants. To ease into lower absorbency training pants, a child may begin by wearing a training pant having a visual wetness indicator and then switch to a training pant having a tactile wetness indicator. Ways of conveying information to the caregiver that may help the caregiver determine the readiness for toilet training as well as the most appropriate training garment for his or her charge may include displays, posters, computer programs, brochures, package literature, shelf information, videos, information on the back of a coupon, or any other suitable form of communication. The information could be available at stores, on television, in computer-friendly form, in advertisements, or any other appropriate venue.

As another example of information that may be provided for the purchaser, a progress scale may be presented to evaluate a child's toilet training progress at a particular point in time. Feedback in the form of specific toilet training recommendations that match a product from the series to the child's current stage of toilet training may also be made available.

The toilet training progress scale may include a plurality of questions about learned skills related to toilet training and may also include a response format for each question including a plurality of response values, the response values cumulatively generating a toilet training progress value having a range of possible resulting values; dividing the range of possible resulting values into a plurality of sub-ranges representing a plurality of stages of toilet training; generating a plurality of recommendations for improving the effectiveness of the child's toilet training regime; dividing the recommendations into a plurality of unique groups corresponding to the plurality of stages of toilet training; assessing the child's toilet training progress using the toilet training progress scale, including calculating a toilet training progress value for the child; matching the child's toilet training progress value to one of the sub-ranges representing a particular stage of toilet training; selecting the group of recommendations that including recommended pants from the series, corresponds to the child's particular stage of toilet training; and outputting the selected group of recommendations.

The toilet training progress scale is used to assess a child's toilet training progress at a particular point in time, and may be used at different points in time to measure improvement and/or regression during the toilet training process. For example, the progress scale may include a series of questions about learned skills related to toilet training. A caregiver responds to specific questions about the child's toilet training progress. The questions about learned skills may concern, for example, the frequency and location of urination or bowel movements (BM), use of the bathroom, understanding of toilet training terms, activities handled independently by the child, and communications from the child about the need to use the bathroom.

Each question includes a response format having a plurality of response values, such as "yes" or "no." The response values may be textual in nature but are desirably assigned a numerical value, such as 1 for "yes" and 0 for "no." Desirably, the response format or each question includes 3 or more response values, particularly 4 or more response values, and more particularly 5 or more response values. An example of a response format with 3 response values is "never," "sometimes," and "always," which may be assigned numerical values of −1, 0 and 1; 0, 1 and 2; 0, 3 and 5; or the like. Including a greater number of response values allows the strength of response to be measured, for example with qualitative questions such as whether your child knows how to urinate in the potty, and allows a wider number of frequencies to be measured, such as with quantitative questions such as how many times per day does your child sit on the toilet.

The result of the progress scale is a "toilet training progress value" that represents the cumulative value of each of the question response values. The toilet training progress value may consist simply of the sum or the average of the individual question response values. More desirably, the response values are differentially weighted depending upon the significance of the relationship between toilet training and the subject of the question. The differentially weighted response values may then be added together or averaged in order to generate the toilet training progress value. As used herein, the terms "cumulative" and "cumulatively" refer to combining the question response values to obtain the toilet training progress value; they are not limited to a specific mathematical approach for combining the response values.

The toilet training progress value represents a concrete and tangible result that can be used for several useful outcomes, including: evaluating the present stage of toilet training; comparing the effectiveness of two or more different toilet training methods; assessing the performance of different toilet training aids; guiding feedback to caregivers for assisting in the toilet training process, including tips and techniques that are likely to be effective at that stage; and recommending a most appropriate absorbent article or training pant selected from the series.

The range of possible resulting values using the progress scale can be divided into a plurality of sub-ranges that represent various stages of toilet training and/or various types of absorbent articles in the series. By way of illustration, the lowest third of the range of possible resulting values may represent the early stages of toilet training, the highest third of the range of possible resulting values may represent the later or final stages of toilet training, and the middle third of the range of possible resulting values may represent the intermediate stages of toilet training. Alternatively, a greater number of sub-ranges may be used to represent a greater number of stages of toilet training and/or a greater number of types of absorbent articles.

A particularly beneficial aspect of the present invention is that a child's toilet training status can be determined using the progress scale for the purpose of providing appropriate tips and guidance on toilet training. As a child progresses through toilet training, a caregiver faces different issues. For example, very early in the process just determining if the child is ready to begin training is of primary importance. Later in the process, issues such as the child being aware of accidents or learning to let the caregiver know before having an accident are bigger concerns.

By using the progress scale to first assess exactly how far the child has progressed in training, tailored guidance can be dispensed to each caregiver individually. In particular, a variety of recommendations pertaining to toilet training may be divided into unique groups that are particularly appropriate for the enumerated stages of toilet training. The recommendations may additionally be divided into groups taking into consideration the age and gender of the child. The groups may have some common recommendations, but desirably the groups will include recommendations that are specific to the targeted stage of training. Although less desirable, where the recommendations are divided into a large number of groups, a minor percentage of the groups can be identical to one another.

For purposes of the present invention, recommendations related to toilet training that might be provided to a caregiver are divided into four categories: information on toilet training garments and toilet training aids, information on training tips, typical child behaviors to monitor, and recommendations of appropriate absorbent garments designed to accommodate a particular size child during a particular stage of the toilet training process. In one scenario, for example, a caregiver completes the survey and the score indicates that the child is just getting started with toilet training and a pant-like garment having a relatively high absorbent capacity may be most appropriate. The following points might be woven into a feedback message.

- If you haven't yet purchased a potty chair, allow your child to help pick one out at the store. Making your child part of the process helps your child get excited about starting training. (Tips/Guidance for Early Stage)
- Introduce disposable training pants, with a recommended style and/or size. Make a big deal out of them. Explain to your child that these are "Big Kid" pants and Big Kids use the potty. (Training Garments for Early Stage)

In another scenario, a caregiver completes the progress survey and the score indicates that the child is about half complete with toilet training. The following points might be provided as a feedback message.

- Don't be surprised if your child always says "no" when you ask if they need to use the potty. Avoid this standoff by getting your child in a routine of using the potty at regular intervals. Don't ask them if they need to go, just tell them it's time to use the potty. If you want, use an egg timer as a reminder so that the child doesn't blame you for the interruption of play that will happen when it's time to go. (Typical behavior/issue and Tip/Guidance for Middle Stage)
- Children at your child's age and stage may lose interest in training after only a week or two. If this happens, you can try to regain their interest by making sitting on the potty part of a fun, made-up game. If you're using rewards, changing the reward at this point may also help. If these or similar activities don't get your child's attention back, take a break from training. Come back to it in a month or two. (Typical behavior/issue and Tip/Guidance for Middle Stage)
- Including a recommendation of a particular size and/or style of training pant.

The information provided in the present method is particularly suited for use by a caregiver over an electronic communication medium, such as an interactive web-site accessible via the internet. The progress scale may be incorporated, by way of illustration, into a web page that provides instruction and guidance pertaining to toilet training. In particular embodiments, therefore, the method also comprises the steps of: storing the toilet training progress scale on an electronic storage medium; storing the recommendations for improving the effectiveness of the child's toilet training regime on an electronic storage medium; providing a user of an electronic communication medium with access to the progress scale; transmitting data representing response values to a processor; providing instructions to the processor to calculate a toilet training progress value from the transmitted data and select the group of recommendations that corresponds to the child's particular stage of toilet training; and outputting the selected group of recommendations to the user via the electronic communication medium. A computer accessible via the internet could provide the necessary processor and storage medium to carry out this method. Alternatively, a caregiver could complete the progress scale and obtain targeted recommendations using a telephone system.

As can be appreciated, computers and electronic communication media such as the internet are particularly suited to transforming data from the progress scale, representing psychological aspects of a child and physiological development stages of a child, through a series of mathematical calculations into a toilet training progress value. This value can then be used in combination with other parameters, such as the age and gender of the child, to provide tailored recommendations for toilet training.

Another method for improving the effectiveness of a child's toilet training regime measures changes in the toilet training progress value over time and selects particular toilet training recommendations, including recommendations of particular pants in the series, suited for the stage of toilet training and the amount of improvement over time.

Thus, in one embodiment, the method comprises the steps of: assessing the child's toilet training progress at an initial point in time using a toilet training progress scale, the progress scale comprising a plurality of questions about learned skills related to toilet training; calculating a first toilet training progress value for the initial point in time; assessing the child's toilet training progress at a subsequent point in time using the progress scale, the subsequent point in time about four days or more after the initial point in time; calculating a second toilet training progress value for the subsequent point in time; comparing the first and second toilet training progress values to obtain a progress indicator; generating a plurality of recommendations for improving the effectiveness of the child's toilet training regime; dividing the recommendations into a plurality of unique groups corresponding to a plurality of stages of toilet training; selecting one of the groups of recommendations based on the value of one of the toilet training progress values and the value of the progress indicator; and outputting the selected group of recommendations, including a recommendation of a particular pant product from the series that corresponds to the child's toilet training progress.

The progress indicator may comprise, for example, the difference between the first and second toilet training progress values. The magnitude of the difference may then be used to select the appropriate group of toilet training recommendations for the child. When the progress indicator reveals that the child has not improved or has regressed in training, the appropriate group of recommendations might include changing a reward, using an older sibling as a role model, or even terminating training for a while.

This method also embodies the concept that the suitableness of the recommendations will depend in part on the stage of training of the child. In addition to selecting an appropriate group of recommendations based on the value of the progress indicator, the stage of training again should be considered. For example, a different group of recommendations would be warranted for a child at the early stages of training compared to the late stages of training, even when the value of the progress indicator is the same. The method could use either one of the first or second toilet training progress values.

Figure 2:
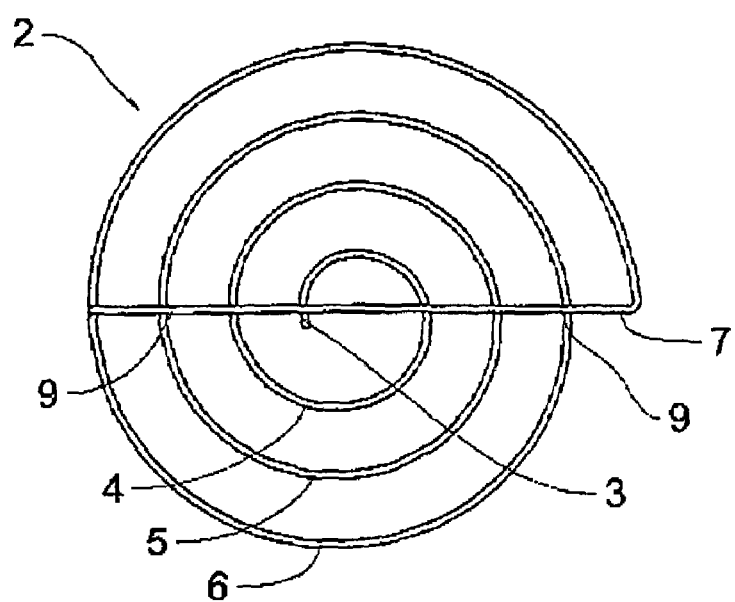
FIG. 2 is a side perspective view of one of a series of absorbent garments, according to one embodiment of this invention.

A detailed drawing of one of the training pants 20 of the invention is shown in FIG. 2, with the training pant 20 in a partially fastened condition. The training pant 20 includes a chassis 32 and may also include a fastening system 80. The chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. As shown in further detail in FIGS. 3 and 4, the chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

The illustrated chassis 32 includes a somewhat rectangular composite structure 33, a pair of transversely opposed front side panels 34, and a pair of transversely opposed back side panels 234. The composite structure 33 and side panels 34 and 234 may be integrally formed, as shown in FIG. 1, or may include two or more separate elements, as shown in FIGS. 3 and 4. The illustrated composite structure 33 includes an outer cover 40, a bodyside liner 42 which is connected to the outer cover in a superposed relation, and an absorbent assembly 44 (FIG. 4) which is positioned or located between the outer cover 40 and the bodyside liner 42. The composite structure 33 may also include a pair of containment flaps 46, as shown in FIG. 4. The rectangular composite structure 33 has opposite linear end edges 45 that form portions of the front and back waist edges 38 and 39, and opposite linear or curvilinear side edges 47 that form portions of the side edges 36 of the chassis 32 (FIGS. 3 and 4). For reference, arrows 48 and 49 depicting the orientation of the longitudinal axis and the transverse axis, respectively, of the training pant 20 are illustrated in FIGS. 3 and 4.

The outer cover 40 has a surface area indicative of the size of the pant 20. Thus, among the training pants 20 within the series, the surface area of the outer cover 40 may increase from the early stage training pant 120 through the later stage training pant 124 or may remain about the same from one stage to the next.

With the training pant 20 in the fastened position as partially illustrated in FIG. 2, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 234 include the portions of the training pant 20 which, when worn, are positioned on the hips of the wearer.

The front region 22 of the chassis 32 includes the transversely opposed front side panels 34 and a front center panel 35 (FIGS. 3 and 4) positioned between and interconnecting the side panels, along with a front waist elastic member 54 and any other connected components. The back region 24 of the chassis 32 includes the transversely opposed back side panels 234 and a back center panel 135 (FIGS. 3 and 4) positioned between and interconnecting the side panels, as well as a rear waist elastic member 56 and any other connected components. The waist edges 38 and 39 of the chassis 32 are configured to encircle the waist of the wearer when worn and provide the waist opening 50 which defines a waist perimeter dimension. Portions of the transversely opposed side edges 36 in the crotch region 26 generally define the leg openings 52.

The chassis 32 is configured to contain and/or absorb any body exudates discharged from the wearer. For example, the chassis 32 desirably, although not necessarily, includes the pair of containment flaps 46 which are configured to provide a barrier to the transverse flow of body exudates. A flap elastic member 53 (FIG. 4) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the chassis 32, and can extend longitudinally along the entire length of the chassis or may only extend partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members 58, as are known to those skilled in the art (FIG. 4). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 234.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the wearer's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 available from available from Uniqema Inc., a division of ICI of New Castle, Del., U.S.A. and GLUCOPON® 220 UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

In accordance with one embodiment of this invention, the absorbent assembly 44, as shown in FIG. 4, is positioned or located between the outer cover 40 and the bodyside liner 42, which components can be joined together by any suitable means, such as adhesives, as are well known in the art. Since the absorbent capacity may vary from pant to pant in the series, the absorbent assembly 44 also may vary from pant to pant in the series. The absorbent assembly may vary by thickness, mass, and/or composition. For example, the absorbent assembly 44 of the later stage training pant 124 is suitably thinner, of lower mass, and/or includes a less absorbent composition compared to the earlier stage training pants 120. Bladder capacity is variable, as is bladder fullness at voiding. Children may be ready for toilet training at different ages and different sizes, and may not progress linearly through the stages of training. Accordingly, a wide range of absorbent capacities among the training pants in the series is suitable.

Absorbent capacity of the absorbent article 20 is based on the anticipated insult volume of a single void. Absorbent capacity can be measured according to the Saturation Capacity Test Method, described below. The absorbent capacity of the garment 20 can be adjusted to accommodate insults across a wide range of user positions, including standing, sitting and prone. Examples of suitable absorbent capacities may range as high as three times the median anticipated insult size for early or middle stage training pants 120, 122, down to less than twice the median anticipated single void volume or less for later stage training pants 124. For example, the series of training pants 20 can be designed and produced to accommodate children between about 18 months and about 48 months old, with insult volumes from 30 ml to 180 ml, or from less than 50 ml to 150 ml, and higher if necessary. Anticipated single void insult size is typically less than 60 ml but can be greater than 100 ml.

This absorbent article capacity and product design provides better leakage performance than cloth training pants or underwear, with low leakage probabilities for insults below the anticipated single void volume. When leaks do occur, the severity of the leak is kept at a manageable level. Leakage performance of the product is enhanced by the containment flaps 46 and the leg elastics 58.

An absorbent assembly 44 including a fluff pulp and superabsorbent material, for example, possibly in combination with other components, is able to retain a specific amount of fluid that is determined by the individual fluid capacities of the components and their relative percentages within the absorbent structure 44. The superabsorbent material, or superabsorbent polymer (SAP), is highly efficient, whereas the fluff pulp material is moderately efficient. An "efficient" absorbent structure will retain a relatively large volume of fluid, whereas an "inefficient" absorbent structure will retain a relatively small volume of fluid.

The absorbent assembly 44 can be any structure which is generally compressible, conformable, non-irritating to the wearer's skin, and capable of absorbing and retaining liquids and certain body wastes at the levels discussed herein. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

Particularly in the later stage training pant 124, the absorbent assembly 44 can include an extremely thin absorbent composite material sold under the trade name NOVATHIN® available from EAM Corporation located in Jessup, Ga., U.S.A., and/or an ultra-thin-absorbent (UTA) material including a mixture of SAP and pulp fiber. An example of a suitable UTA may include 3.7 grams (g) of FAVOR® SXM 9543 SAP, available from Stockhausen GmbH & Co. KG located in Krefeld, Fed. Rep. of Germany, and 3.7 g of NB416 pulp fiber available from Weyerhauser located in Federal Way, Wash., with the sample's mass contained in an area of 0.037 square meters, with a density of 0.33 grams per cubic centimeter.

In one embodiment, the absorbent assembly 44 can be generally rectangular in shape, and can include a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly 44. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly 44.

The chassis 32 can also incorporate other materials that are designed primarily to receive, temporarily store, and/or transport liquid along the mutually facing surface with the absorbent assembly 44, thereby maximizing the overall absorbent capacity of the absorbent assembly 44, if desired. One suitable material is referred to as a surge layer (not shown) and includes a material having a basis weight of about 50 to about 120 grams per square meter (gsm), and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A. Another example of a suitable surge layer may include a material made of 6 denier polyethylene terephthalate (PET) and 6 denier bicomponent binder fiber, having a basis weight of about 50 to about 120 gsm.

As noted previously, the illustrated training pant 20 has front and back side panels 34 and 234 disposed on each side of the chassis 32. These transversely opposed front side panels 34 and transversely opposed back side panels 234 can be permanently bonded to the composite structure 33 of the chassis 32 in the respective front and back regions 22 and 24, and can be releasably attached to one another by a fastening system 80. Alternatively, instead of being releasably attachable, the front and back side panels 34, 234 can be permanently bonded to one another, respectively, to create a non-refastenable pant.

As shown best in FIGS. 3 and 4, the front side panels 34 can be permanently bonded to and extend transversely beyond the linear side edges 47 of the composite structure 33 in the front region 22 along attachment lines 66, and the back side panels 234 can be permanently bonded to and extend transversely beyond the linear side edges of the composite structure in the back region 24 along attachment lines 66. The side panels 34 and 234 may be attached using attachment means known to those skilled in the art such as adhesive, thermal or ultrasonic bonding. The side panels 34 and 234 can also be formed as a portion of a component of the composite structure 33, such as the outer cover 40 or the bodyside liner 42.

In particular embodiments for improved fit and appearance, the side panels 34 and 234 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 234 desirably have an average length dimension of about 10 centimeters or greater, such as about 15 centimeters. While each of the side panels 34 and 234 extend from the waist opening 50 to one of the leg openings 52, the back side panels 234 have a continually decreasing length dimension moving from the attachment line 66 to a distal edge 68b of the back panel 234, as is best shown in FIGS. 3 and 4.

Each of the side panels 34 and 234 can include one or more individual, distinct pieces of material. In particular embodiments, for example, each side panel 34 and 234 can include first and second side panel portions that are joined at a seam, with at least one of the portions including an elastomeric material. Still alternatively, each individual side panel 34 and 234 can include a single piece of material which is folded over upon itself along an intermediate fold line (not shown).

The side panels 34 and 234 desirably include an elastic material capable of stretching in a direction generally parallel to the transverse axis 49 of the training pant 20. In particular embodiments, the front and back side panels 34 and 234 may each include an interior portion 78 disposed between the distal edge 68a, 68b and the respective front or back center panel 35 or 135. In the illustrated embodiment in FIG. 4, the interior portions 78 are disposed between the distal edges 68a, 68b and the side edges 47 of the rectangular composite structure 33. The elastic material of the side panels 34 and 234 can be disposed in the interior portions 78 to render the side panels elastomeric in a direction generally parallel to the transverse axis 49. Most desirably, each side panel 34 and 234 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. No.: 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al., all of which are incorporated herein by reference. Alternatively, the side panel material may include other woven or nonwoven materials, such as those described above as being suitable for the outer cover 40 or bodyside liner 42, or stretchable but inelastic materials.

As mentioned, the training pant 20 according to the present invention may include a fastening system 80 for securing the training pant about the waist of the wearer (FIG. 2). The illustrated fastening system 80 may include fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549. In one embodiment, the outer cover material and/or the body side liner material may serve as a loop type fastener.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils). In one embodiment, the outer cover material and/or the body side liner material may serve as a hook type fastener.

As described herein, the various components of the absorbent garment 20 can be integrally assembled together employing various types of suitable attachment means, such as adhesive, sonic and thermal bonds or combinations thereof. The resulting product is a series of absorbent garments having varying levels of absorbency. The garments in the series may vary only by levels of absorbency, or may vary in terms of other features such as structure, size, or special features such as wetness indicators.

Saturated Capacity Test Method

Saturated capacity is determined using a Saturated Capacity (SAT CAP) Tester with Magnahelic vacuum gage and latex dam: Referring to FIGS. 5-7, a Saturated Capacity tester vacuum apparatus 110 comprises a vacuum chamber 112 supported on four leg members 114. Vacuum chamber 112 includes a front wall member 116, a rear wall member 118 and two side walls 120 and 121. The wall members are about 0.5 inch thick, and are constructed and arranged to provide a chamber having outside dimensions measuring 23.5 inches in length, 14 inches in width and 8 inches in depth. A vacuum pump (not shown) operably connects with vacuum chamber 112 through an appropriate vacuum line conduit and vacuum valve 124. In addition, a suitable air bleed line connects into vacuum chamber 112 through air bleed valve 126. A hanger assembly 128 is suitably mounted on rear wall 118 and is configured with S-curved ends to provide a convenient resting place for supporting latex dam sheet 130 in a convenient position away from the top of vacuum apparatus 110. A suitable hanger assembly can be constructed from 0.25 inch diameter stainless steel rod. Latex sheet 130 is looped around dowel member 132 to facilitate grasping and allow a convenient movement and positioning of the latex sheet. In the illustrated position, dowel member 132 is shown supported in hanger assembly 128 to position the latex sheet 130 in an open position away from the top of vacuum chamber 112. A bottom edge of latex sheet 130 is clamped against a rear edge support member 134 with suitable securing means, such as toggle clamps 140. The toggle clamps are mounted on rear wall member 118 with suitable spacers 141 which provide an appropriate orientation and alignment of the toggle clamps for the desired operation. Three support shafts 142 are 0.75 inch in diameter and are removably mounted within vacuum chamber 112 by means of support brackets 144. The support brackets are generally equally spaced along front wall member 116 and rear wall member 118 and arranged in cooperating pairs. In addition the support brackets are constructed and arranged to suitably position the uppermost portions of support shafts 142 flush with the top of the front, rear and side wall members of vacuum chamber 112. Thus, support shafts 142 are positioned substantially parallel with one another and are generally aligned with side wall members 120 and 121. In addition to rear edge support member 134, the tester apparatus includes a front support member 136 and two side support members 138 and 139. Each edge support member measures about 1 inch in width and about 1.25 inches in height. The lengths of the support members are constructed to suitably surround the periphery of the open top edges of vacuum chamber 112, and are positioned to protrude above the top edges of the chamber wall members by a distance of about 0.5 inch. A layer of egg crating type material 146 is positioned on top of support shafts 142 and the top edges of the wall members of vacuum chamber 112. The egg crate material extends over a generally rectangular area measuring 23.5 inches by 14 inches, and has a depth measurement of about 0.38 inches. The individual cells of the egg crating structure measure about 0.5 inch square, and the thin sheet material comprising the egg crating is composed of a suitable material, such as polystyrene. For example, the egg crating material can be McMaster Supply Catalog No. 162 4K 14, translucent diffuser panel material. A layer of 0.19 mesh nylon screening 148, which measures 23.5 inches by 14 inches, is placed on top of egg crating material 146. A suitable drain line and drain valve 150 connects to bottom plate member 119 of vacuum chamber 112 to provide a convenient mechanism for draining liquids from the vacuum chamber. The various wall members and support members of tester 110 may be composed of a suitable non-corroding, moisture-resistant material, such as polycarbonate plastic. The various assembly joints may be affixed by solvent welding, and the finished assembly of the tester is constructed to be watertight. A vacuum gauge 152 operably connects through a conduit into vacuum chamber 112. A suitable pressure gauge is a Magnahelic differential gauge capable of measuring a vacuum of 0-100 inches of water, such as a No. 2100 gauge available from Dwyer Instrument Incorporated.

The dry product or other absorbent structure is weighed and then placed in excess 0.9% saline solution and allowed to soak for 20 minutes. After the 20 minute soak time, the absorbent structure is placed on the egg crate material and mesh nylon screening of the Saturated Capacity Tester. The latex sheet is placed over the absorbent structure(s) and the entire egg crate grid so that the sheet creates a seal when vacuum is drawn on the Tester. A vacuum of 0.5 pounds per square inch (psi) is held in the Saturated Capacity Tester for five minutes. The vacuum creates a pressure on the absorbent structure(s), causing drainage of some liquid. After five minutes at 0.5 psi vacuum, the latex sheet is rolled back and the absorbent structure(s) are weighed to generate a wet weight. The overall capacity of each absorbent structure is determined by subtracting the dry weight of each absorbent from the wet weight of that absorbent determined at this point in the procedure. The 0.5 psi SAT CAP or SAT CAP of the absorbent structure is determined by the following formula: (wet weight−dry weight)/(dry weight). The SAT CAP value has units of grams fluid/gram absorbent. For both overall capacity and SAT CAP, a minimum of four specimens of each sample should be tested, and the results averaged. If the absorbent structure has low integrity or disintegrates during the soak or transfer procedures, the absorbent structure can be wrapped in a containment material such as paper toweling, for example HI-DRI® paper towels manufactured by Kimberly-Clark Corporation, Neenah, Wis. The absorbent structure can be tested with the overwrap in place, and the capacity of the overwrap can be independently determined and subtracted from the wet weight of the total wrapped absorbent structure to obtain a wet absorbent weight.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A method of concurrently providing a series of types of training pants to consumers, comprising:
   providing a first sub-series of disposable pant-like garments, wherein the first sub-series includes a first garment type in at least two different sizes designed to fit wearers in at least two different size ranges, the first garment type having a first level of absorbency for a first garment size and a first level of absorbency for a second garment size, wherein the second garment size is larger than the first garment size; and
   providing a second sub-series of disposable pant-like garments, wherein the second sub-series includes a second garment type in at least two different sizes, namely a third garment size and a fourth garment size that is larger than the third garment size, each of the third and fourth garment sizes overlapping, at least in part, the size ranges of at least one of the first and second garment sizes in the first sub-series;

each of the garments of the second sub-series having a second level of absorbency for the third garment size and a second level of absorbency for the fourth garment size, wherein the second level of absorbency is lower than the first level of absorbency for a garment in the first sub-series overlapping at least a portion of the same size range; and each of the garments in the first sub-series is adapted for a first stage of toilet training, and each of the garments in the second sub-series is adapted for a second stage of toilet training subsequent to the first stage.

2. The method of claim 1, further comprising conveying information to a consumer that provides guidance to the consumer in selecting an appropriate type of garment from the series for a child in a stage of toilet training.

3. The method of claim 1, wherein the series includes at least one unisex pant-like garment, and at least one gender-specific pant-like garment.

4. The method of claim 3, wherein the gender-specific pant-like garment is the second type of garment.

5. The method of claim 1, wherein the series includes at least one garment type having a first wetness indicator, and at least one garment type having a second wetness indicator of a different type than the first wetness indicator.

6. The method of claim 1, wherein the series includes at least one garment type having a tactile wetness indicator, and at least one garment type having a visual wetness indicator.

7. The method of claim 6, wherein the first type of garment includes a visual wetness indicator, and the second type of garment includes a tactile wetness indicator.

8. The method of claim 1, wherein the first sub-series includes the first garment type in at least three different sizes.

9. The method of claim 1, wherein the first level of absorbency for the first garment size is the same as the first level of absorbency for the second garment size, and the second level of absorbency for the third garment size is the same as the second level of absorbency for the fourth garment size.

10. The method of claim 1, wherein the first level of absorbency for the first garment size is different than the first level of absorbency for the second garment size, and the second level of absorbency for the third garment size is different than the second level of absorbency for the fourth garment size.

11. A method of concurrently providing a series of types of training pants to consumers, comprising:

providing a first sub-series of disposable pant-like garments, wherein the first sub-series includes a first garment type in at least two different sizes designed to fit wearers in at least two different weight ranges, the first garment type having a first absorbent capacity for a first garment size and a first absorbent capacity for a second garment size, wherein the second garment size is larger than the first garment size; and providing a second sub-series of disposable pant-like garments, wherein the second sub-series includes a second garment type in at least two different sizes, namely a third garment size and a fourth garment size that is larger than the third garment size, each of the third and fourth garment sizes overlapping, at least in part, the weight ranges of at least one of the first and second garment sizes in the first sub-series;

each of the garments of the second sub-series having a second absorbent capacity for the third garment size and a second absorbent capacity for the fourth garment size, wherein the second absorbent capacity is lower than the first absorbent capacity for a garment in the first sub-series overlapping at least a portion of the same weight range, and each of the garments in the first sub-series is adapted for a first stage of toilet training, and each of the garments in the second sub-series is adapted for a second stage of toilet training subsequent to the first stage.

12. The method of claim 11, further comprising conveying information to a consumer that provides guidance to the consumer in selecting an appropriate type of garment from the series for a child in a stage of toilet training.

13. The method of claim 11, wherein the series includes at least one unisex pant-like garment, and at least one gender-specific pant-like garment.

14. The method of claim 13, wherein the gender-specific pant-like garment is the second garment type.

15. The method of claim 11, wherein the series includes at least one garment type having a first wetness indicator, and at least one garment type having a second wetness indicator of a different type than the first wetness indicator.

16. The method of claim 11, wherein the series includes at least one garment type having a tactile wetness indicator, and at least one garment type having a visual wetness indicator.

17. The method of claim 16, wherein the first garment type includes a visual wetness indicator, and the second garment type includes a tactile wetness indicator.

18. The method of claim 11, wherein the first sub-series includes the first garment type in at least three different sizes.

19. The method of claim 11, wherein the first absorbent capacity for the first garment size is the same as the first absorbent capacity for the second garment size, and the second absorbent capacity for the third garment size is the same as the second absorbent capacity for the fourth garment size.

20. The method of claim 11, wherein the first absorbent capacity for the first garment size is different than the first absorbent capacity for the second garment size, and the second absorbent capacity for the third garment size is different than the second absorbent capacity for the fourth garment size.

21. A method of concurrently providing a series of types of training pants to consumers, comprising:

providing a first sub-series of disposable pant-like garments, wherein the first sub-series includes a first garment type in at least a first size and a second size designed to fit wearers in at least a first size range and a second size range, respectively, the first garment type having a first level of absorbency for the first garment size and a first level of absorbency for the second garment size, wherein the second garment size is larger than the first garment size; and providing a second sub-series of disposable pant-like garments, wherein the second sub-series includes a second garment type in at least a third size and a fourth size that is larger than the third size, with the third and fourth sizes each overlapping, at least in part, at least one of the size ranges of the garments in the first sub-series;

each of the garments of the second sub-series having a second level of absorbency for the third garment size and a second level of absorbency for the fourth garment size, wherein the second level of absorbency is lower than the first level of absorbency for a garment in the first sub-series overlapping at least a portion of the same size range; and each of the garments in the first sub-series is adapted for a first stage of toilet training, and each of the garments in the second sub-series is adapted for a second stage of toilet training subsequent to the first stage.

22. The method of claim 21, wherein the series includes a first garment type and a second garment type each having substantially the same size, the first garment type having an absorbent capacity of greater than about 400 grams and the second garment type having an absorbent capacity of less than about 300 grams.

23. The method of claim 21, wherein the series includes at least one garment having a refastenable fastening system for attaching a front portion of the garment to a back portion of the garment, and at least one garment having a pair of permanently bonded side seams for attaching a front portion of the garment to a back portion of the garment.

24. The method of claim 21, wherein the series includes at least one unisex pant-like garment, and at least one gender-specific pant-like garment.

25. The method of claim 21, wherein the series includes at least one garment type having a first wetness indicator, and at least one garment type having a second wetness indicator of a different type than the first wetness indicator.

26. The method of claim 21, wherein the series includes at least one garment type having a tactile wetness indicator, and at least one garment type having a visual wetness indicator.

27. The method of claim 21, wherein the first sub-series includes the first garment type in at least three different sizes.

28. The method of claim 21, wherein the first level of absorbency for the first garment size is the same as the first level of absorbency for the second garment size, and the second level of absorbency for the third garment size is the same as the second level of absorbency for the fourth garment size.

29. The method of claim 21, wherein the first level of absorbency for the first garment size is different than the first level of absorbency for the second garment size, and the second level of absorbency for the third garment size is different than the second level of absorbency for the fourth garment size.

30. A method of providing a series of types of training pants to consumers, comprising:

providing a first series of disposable pant-like garments, wherein the first series includes at least three garments designed to fit wearers of different sizes, the garments of the first series having a first level of absorbency for a first garment size, a first level of absorbency for a second garment size, and a first level of absorbency for a third garment size, wherein the third garment size is larger than the second garment size, and the second garment size is larger than the first garment size; and providing a second series of disposable pant-like garments, wherein the second series includes at least two garments in at least two different sizes, namely a fourth size and a fifth size, wherein the fifth size is larger than the fourth size, each of the garments in the second series overlapping in size, at least in part, the size range of at least one of the garments in the first series;

each of the garments of the second series having a second level of absorbency for the fourth garment size and a second level of absorbency for the fifth garment size, wherein the second level of absorbency is lower than the first level of absorbency for a garment in the first series overlapping at least a portion of the same size range.

31. The method of claim 30, wherein the garments in one of the series include a first wetness indicator, and the garments in another one of the series include a second wetness indicator of a different type than the first wetness indicator.

32. The method of claim 30, wherein the garments in one of the series include a tactile wetness indicator, and the garments in another one of the series include a visual wetness indicator.

33. The method of claim 30, wherein the first level of absorbency for the first garment size is the same as the first level of absorbency for the second garment size and the first level of absorbency for the third garment size, and the second level of absorbency for the fourth garment size is the same as the second level of absorbency for the fifth garment size.

34. The method of claim 30, wherein the first level of absorbency for the first garment size is different than the first level of absorbency for the second garment size and the first level of absorbency for the third garment size, and the second level of absorbency for the fourth garment size is different than the second level of absorbency for the fifth garment size.

* * * * *